United States Patent
Barany et al.

(10) Patent No.: US 7,077,142 B1
(45) Date of Patent: Jul. 18, 2006

(54) INTRAVENOUS RETAINMENT IMMOBILIZER FOR CHILDREN

(76) Inventors: Paula Barany, 9099 Harvard Blvd., Poland, OH (US) 44514; Joann G. Miller, 48429 State Route 14, New Waterford, OH (US) 44445

( * ) Notice: Subject to any disclaimer, the term of this patent is extended or adjusted under 35 U.S.C. 154(b) by 0 days.

(21) Appl. No.: 10/974,995

(22) Filed: Oct. 28, 2004

(51) Int. Cl.
 *A61F 5/37* (2006.01)
(52) U.S. Cl. .................. 128/877; 604/174; 604/179
(58) Field of Classification Search ............. 128/877; 604/174, 179
See application file for complete search history.

(56) References Cited

U.S. PATENT DOCUMENTS

| 4,043,330 | A |   | 8/1977  | Bansal |          |
|-----------|---|---|---------|--------|----------|
| 4,531,942 | A | * | 7/1985  | Turner | 604/180  |
| 5,018,534 | A |   | 5/1991  | Grant  |          |
| 5,076,289 | A | * | 12/1991 | Darling | 128/877 |
| 5,083,575 | A | * | 1/1992  | Jones  | 128/877  |
| 5,131,412 | A | * | 7/1992  | Rankin | 128/877  |
| 5,269,322 | A | * | 12/1993 | Mandel | 128/845  |
| 5,339,834 | A | * | 8/1994  | Marcelli | 128/877 |
| 5,682,905 | A |   | 11/1997 | Grant  |          |
| 5,728,053 | A | * | 3/1998  | Calvert | 602/5   |

* cited by examiner

*Primary Examiner*—Henry Bennett
*Assistant Examiner*—Camtu Nguyen
(74) *Attorney, Agent, or Firm*—Harpman & Harpman

(57) ABSTRACT

An intravenous catheter retainment device for use on young children and babies that supports and overlies a portion of the forearm and hand having an inserted intravenous needle therewithin. An overlying portion of said cover is of a stretchable see through netting that conforms to the hand and lower forearm securely holding it in place on a rigid support board. The netting allows for visual inspection of the IV site and is releasably secured to the support board for ease of selected access thereto.

6 Claims, 3 Drawing Sheets

INTRAVENOUS RETAINMENT IMMOBILIZER FOR CHILDREN

BACKGROUND OF THE INVENTION

1. Field of the Invention

This invention relates to medical equipment and more specifically to restraint devices for intravenous injection needles that are inserted beneath the skin into a vein of a patient and is secured to the patient by adhesive materials.

2. Description of Prior Art

Prior art devices of this type have been directed to a variety of ways to immobilize a patient's arm and help retain intravenous catheters in position used to supply medications and fluids to a patient. Heretofore, the primary emphasis has been on adults in which numerous so-called IV shields and retainers have been developed; see for example U.S. Pat. Nos. 4,043,330, 5,018,534, 5,083,575, 5,339,834 and 5,682,905.

In U.S. Pat. No. 4,043,330 an arm board for an IV patient is described having a padded board with a pair of retainment straps extending therefrom.

U.S. Pat. No. 5,018,534 is directed to an IV catheter shield and retainer in which a slotted board is provided having a plurality of engagement straps and a transparent rigid housing that is pivotally positioned thereon.

In U.S. Pat. No. 5,083,575 a child's IV board having a two-part configuration that engages the lower forearm of the child and an independent hand immobilizer with an adjustable transparent cover.

An infusion site cover and immobilizer can be seen in U.S. Pat. No. 5,339,834 having a two-part configuration with a base element and a registerably positionable open cylindrical top section that is retained by straps extending from the base.

U.S. Pat. No. 5,682,905 claim an intravenous injection shield assembly having a base with sidewalls that are contoured to extend over the patient's hand.

SUMMARY OF THE INVENTION

A pediatric intravenous arm and hand retainment device that is adjustably secured on the lower forearm and hand of a small child or baby. The restraint device has a rigid support board with an attached flexible netting extending therefrom that is stretched over the child's arm and hand immobilizing and protecting an inserted IV catheter and provides for visual inspection of the IV site and can be easily accessed.

DETAILED DESCRIPTION OF THE INVENTION

Figure 1:
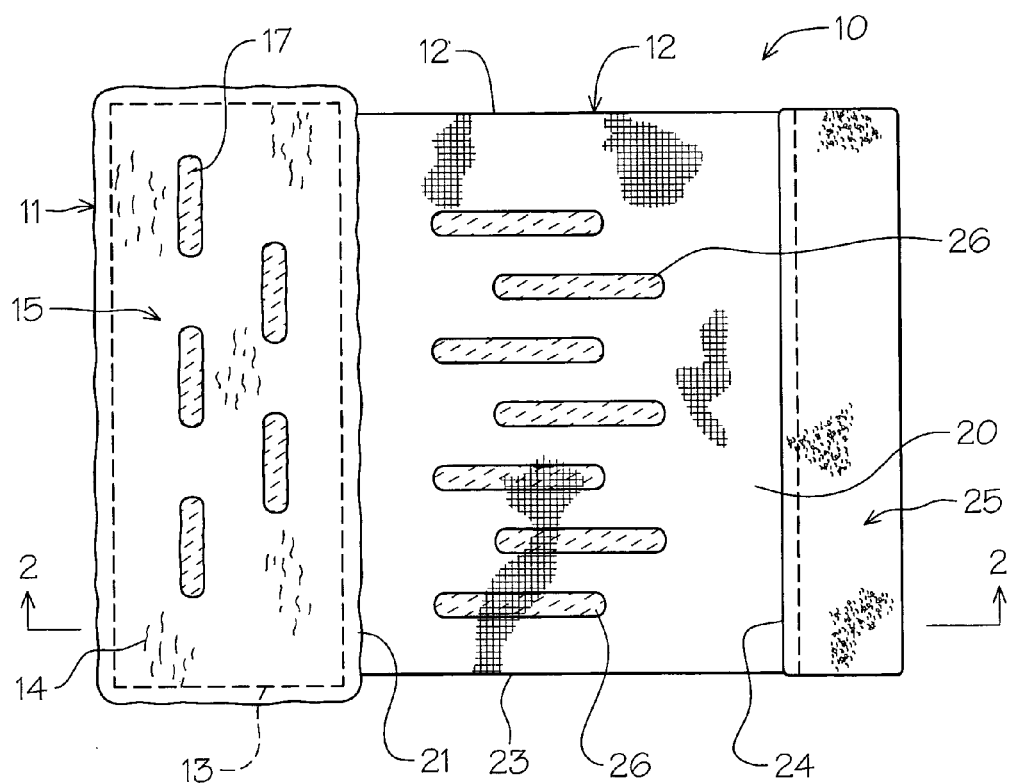
FIG. 1 is a top plan view of the pediatric intravenous restraint device of the invention.
Figure 2:
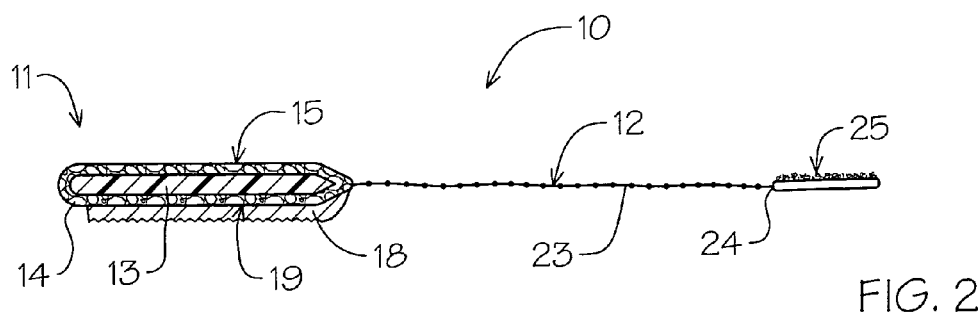
FIG. 2 is a cross-sectional view on lines 2—2 of FIG. 1.

Referring to FIGS. 1 and 2 of the drawings, a pediatric IV retainment cover 10 of the invention can be seen having a generally rectangular rigid base portion 11 with a flexible retainment cover portion 12 extending therefrom. The base portion 11 has a rigid panel 13 within a cushion fabric cover 14. The fabric cover 14 can be of natural or synthetic material and preferably encapsulates the panel 13 by conventional means. This encapsulated panel combination provides for a stable, comfortable rigid surface 15 on which the infant's forearm 16 and hand 16A can be positioned, as best seen in FIGS. 4 and 5 of the drawings.

Figure 3:
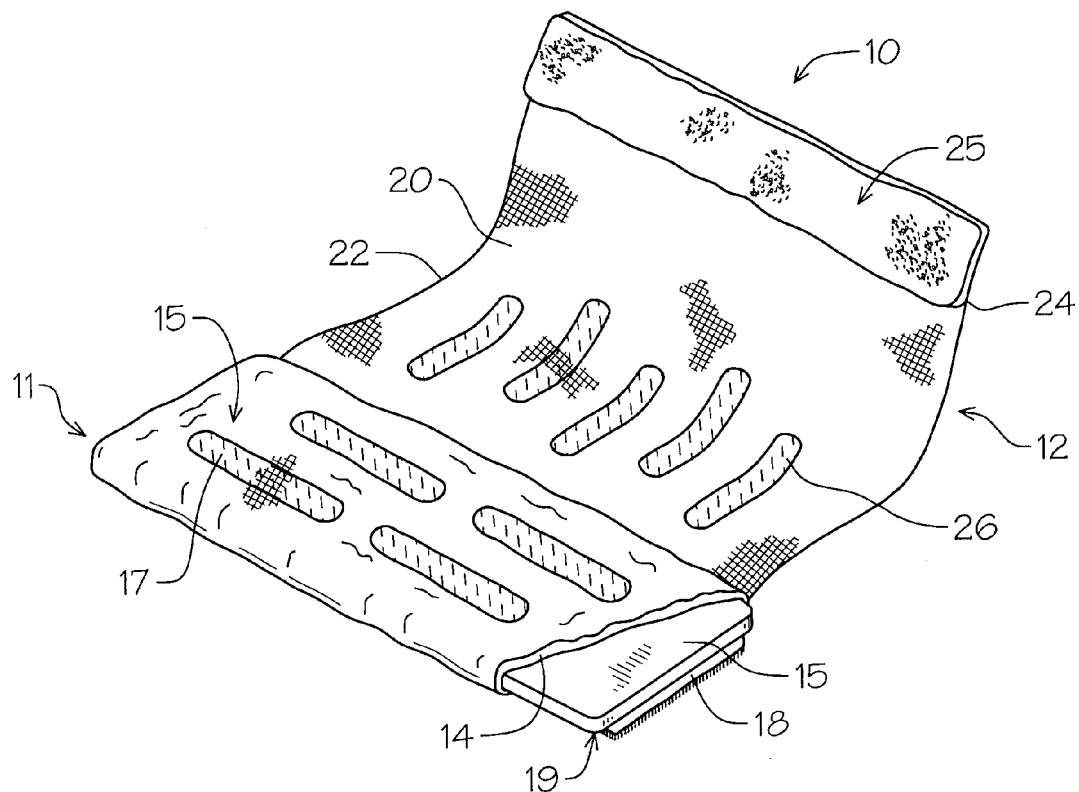
FIG. 3 is a perspective view of the intravenous restraint device of the invention with a portion cut-away.

A plurality of enhanced friction engagement areas 17 are provided on the upper engagement surface 15 of the fabric cover 14. The frictional engagement areas 17 can be of a variety of friction enhancing material preferably as an example, an imprintable coating such as "super gel ink" 180 series brand manufactured by One Stroke, Inc., of Louisville, Ky. which is readily available and can be applied to porous and non-porous material and has the added benefit of allowing for letter indicia (not shown) to be used. Such gel ink imprinting is well known and understood by those skilled in the art and provides for enhanced frictional co-efficient to help stabilize the infant's forearm 16 and hand 16A positioned thereon. An area of hook type material 18, of hook and loop material such as Velcro brand, is applied to an underside 19 of the base portion 11 in oppositely disposed relation to hereinbefore described upper arm and hand engagement surface 15, as best seen in FIGS. 2 and 3 of the drawings.

The flexible restraint cover portion 12 is comprises of a sheet of synthetic elastic netting 20 extending from and secured to the fabric cover 14 integrally along a longitudinal side edge 21 thereof. The netting 20 has a parallel space longitudinal edges 22 and 23 and a transverse end edge at 24. A strip of fabric loop type fastening material 25 of Velcro brand is secured preferably by stitching along the terminus end edge at 24 and is of a corresponding overall dimension to that of the hereinbefore described hook type fastening material 18 on the underside surface 19 of the base portion 11 for registrationable engagement therewith as will be described in greater detail hereinafter.

Figure 4:
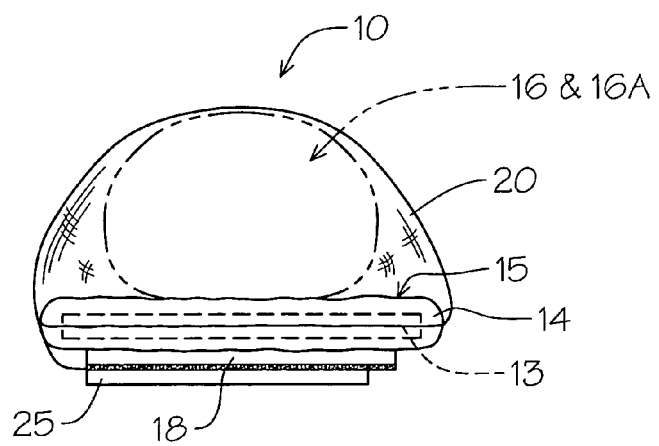
FIG. 4 is an end elevational view of the invention in use on a patient shown in broken lines.
Figure 5:
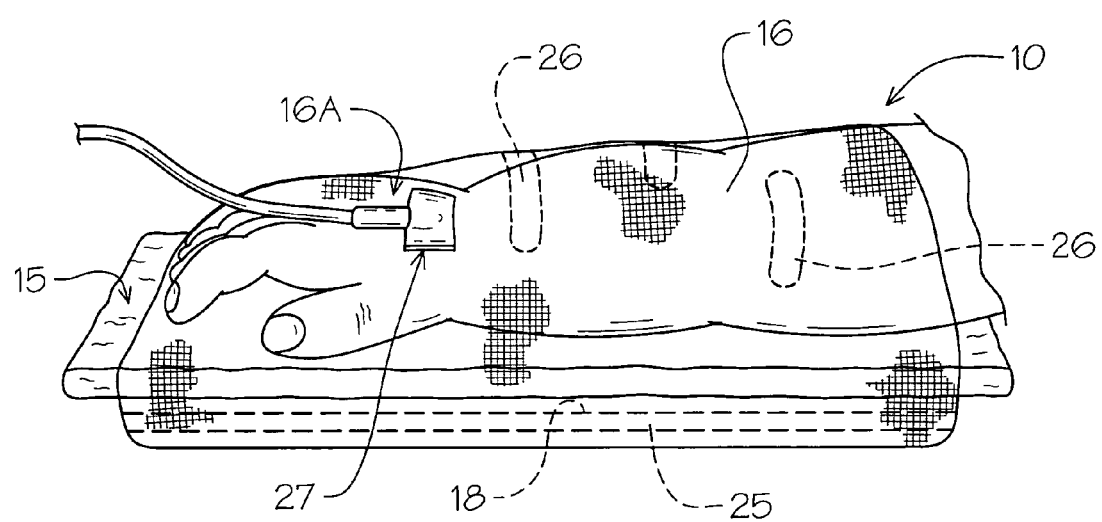
FIG. 5 is a perspective view of the invention in use.

Additional areas 26 of enhances frictional co-efficient material "super gel ink" as previously disclosed may also be applied to the netting 20 so as to correspond for engagement with the infant's forearm and hand 16 and 16A when pulled thereover and releasably secured in place by the interlocking hook 18 and loop 25 material as best seen in FIGS. 4 and 5 of the drawings. It will be evident from the above description that the elastic netting 20 will conform about the irregular contours associated with the infant's hand 16A and forearm portion 16 stabilizing them in place on the base portion 11. Also given the physical properties of the netting 20, an intravenous (IV) needle 27 and area thereabout can be easily seen and accessed assuring the proper intake of the IV 27 is being maintained. The netting 20, as noted, will stabilize the infant's arm 16 and hand 16A as well as consolidate over the IV 26 assuring its placement is maintained in a tamper resistant covering configuration.

It will be evident that ease of access to the IV 26 is assured by simple disengagement of the interlocking hook 18 and loop 25 material as required and also visual inspection can be assured due to the semi-transparent nature of the netting 20, as noted.

Given the nature of the materials used, construction of the pediatric IV restraint and inspection cover 10 can be disposable to effectively maintain a hygienic environment for the patient.

It will thus be seen that a new and novel pediatric IV retainment and inspection cover 10 has been illustrated and described and that various changes and modifications may be made therein without departing from the spirit of the invention.

We claim:

1. A pediatric restraint cover for protecting the position of an intravenous needle assembly when inserted into a body part of an infant comprising, an elongated rectangular rigid base portion for receiving a portion of the infant's limb thereon, a cushion cover extending about said base portion, said cushion cover defining an upper body part engagement surface with spaced oppositely disposed longitudinal side edges, a flexible elastic netting sheet extending continuously from one of said side edges for securing said base portion to an infant's limb positioned thereon, multiple areas of increased frictional co-efficiency material on said netting sheet, a first fastener means on said netting sheet in spaced parallel relation to one of said cover's side edges, a second fastener means on said cushion cover in oppositely disposed relation to said upper body part engaged surface for registerable engagement with said first fastener means.

2. The pediatric restraint cover set forth in claim 1 wherein said cushion cover is of a fabric sleeve secured together around its perimeter edges.

3. The pediatric restraint cover set forth in claim 1 wherein said netting sheet is of a known transverse dimension equal to that of said covers longitudinal side edges and allows visual inspection of said intravenous needle assembly and said infant's body part.

4. The pediatric restraint cover set forth in claim 1 wherein said first fastening means on said netting sheet is of a hook and loop fabric fastener material.

5. The pediatric restraint cover set forth in claim 1 wherein said second fastening means on said cushion cover is of a hook and loop fabric fastener material.

6. The pediatric restraint cover set forth in claim 1 wherein the surface for receiving said portion of said infants limb thereon has areas of increased frictional co-efficiency.

\* \* \* \* \*